US010366792B2

(12) United States Patent
Brauner et al.

(10) Patent No.: US 10,366,792 B2
(45) Date of Patent: Jul. 30, 2019

(54) SYSTEM AND METHOD FOR DETECTING RETINA DISEASE

(71) Applicant: Bio-Tree Systems, Inc., Framingham, MA (US)

(72) Inventors: Raul A. Brauner, Framingham, MA (US); Kongbin Kang, Providence, RI (US); Yanchun Wu, Sharon, MA (US)

(73) Assignee: Bio-Tree Systems, Inc., Framingham, MA (US)

( * ) Notice: Subject to any disclaimer, the term of this patent is extended or adjusted under 35 U.S.C. 154(b) by 0 days.

(21) Appl. No.: 15/581,315

(22) Filed: Apr. 28, 2017

(65) Prior Publication Data

US 2017/0316165 A1  Nov. 2, 2017

Related U.S. Application Data

(60) Provisional application No. 62/330,297, filed on May 2, 2016, provisional application No. 62/330,337, filed on May 2, 2016.

(51) Int. Cl.
| | |
|---|---|
| *G06K 9/00* | (2006.01) |
| *G16H 50/20* | (2018.01) |
| *G06T 7/00* | (2017.01) |
| *G06F 19/00* | (2018.01) |
| *G16H 50/50* | (2018.01) |

(52) U.S. Cl.
CPC ............. *G16H 50/20* (2018.01); *G06F 19/00* (2013.01); *G06F 19/321* (2013.01); *G06T 7/0012* (2013.01); *G16H 50/50* (2018.01)

(58) Field of Classification Search
None
See application file for complete search history.

(56) References Cited

U.S. PATENT DOCUMENTS

| 6,535,623 | B1 | 3/2003 | Tannenbaum et al. |
| 8,687,862 | B2 * | 4/2014 | Hsu ..................... G06K 9/0061 |
| | | | 341/79 |

(Continued)

FOREIGN PATENT DOCUMENTS

| JP | 10-243924 A | 9/1998 |
| WO | 2006/085254 A1 | 8/2006 |
| WO | 2008/002648 A2 | 1/2008 |

OTHER PUBLICATIONS

Final rejection dated Oct. 30, 2017 in co-pending U.S. Appl. No. 14/692,342.

(Continued)

*Primary Examiner* — Samah A Beg
(74) *Attorney, Agent, or Firm* — Nields, Lemack & Frame, LLC

(57) ABSTRACT

A system and method for diagnosing retina disease is disclosed. The method comprises capturing a plurality of images of the vascular network within the retina, such as through the use of optical coherence tomography (OCT). This plurality of images are then processed to determine the location and diameter of each vessel in the three-dimensional vascular network in the retina. The vascular network is then divided into a plurality of equal unit volumes. The vessel density, vascular volume density and other metrics can then be determined for each unit volume. This information can then be used to identify retina disease. The information can be parsed and presented in a variety of ways.

26 Claims, 17 Drawing Sheets

(56) References Cited

U.S. PATENT DOCUMENTS

| | | | |
|---|---|---|---|
| 8,761,466 B2* | 6/2014 | Kang | G06K 9/4609 |
| | | | 382/128 |
| 8,805,051 B2 | 8/2014 | Najarian et al. | |
| 8,879,813 B1* | 11/2014 | Solanki | G06T 7/0014 |
| | | | 382/128 |
| 9,721,341 B2* | 8/2017 | Kang | G06K 9/4609 |
| 9,898,659 B2* | 2/2018 | Kanagasingam | G06T 7/0012 |
| 2003/0176780 A1 | 9/2003 | Arnold et al. | |
| 2006/0029927 A1 | 2/2006 | Johnson et al. | |
| 2008/0260229 A1 | 10/2008 | Mashiach | |
| 2011/0080558 A1* | 4/2011 | Marshall | A61B 5/0059 |
| | | | 351/206 |
| 2012/0027275 A1* | 2/2012 | Fleming | G06F 19/321 |
| | | | 382/128 |
| 2012/0150048 A1* | 6/2012 | Kang | A61B 6/508 |
| | | | 600/481 |
| 2014/0073917 A1 | 3/2014 | Huang et al. | |
| 2015/0302584 A1* | 10/2015 | Brauner | A61B 6/508 |
| | | | 382/128 |
| 2016/0174830 A1* | 6/2016 | Rubin | A61B 3/102 |
| | | | 351/206 |
| 2017/0156582 A1* | 6/2017 | Ehlers | A61B 3/0025 |
| 2017/0278243 A1* | 9/2017 | Kang | A61B 6/5247 |
| 2017/0287131 A1* | 10/2017 | Kang | G06T 7/0012 |
| 2018/0220984 A1* | 8/2018 | Brauner | G06T 7/62 |

OTHER PUBLICATIONS

Canadian communication dated Jan. 22, 2018 in co-pending Canadian patent application No. 2,792,354.

European communication dated Apr. 26, 2018 in co-pending European patent application No. 10749066.6.

International Search Report and Written Opinion dated Jul. 13, 2017 in corresponding PCT application No. PCT/US2017/030069.

Office action dated Oct. 22, 2014 in co-pending U.S. Appl. No. 13/254,913.

Office action dated Jan. 30, 2017 in co-pending U.S. Appl. No. 14/692,342.

Notice of allowance dated Nov. 1, 2018 in co-pending U.S. Appl. No. 14/692,342.

\* cited by examiner

SYSTEM AND METHOD FOR DETECTING RETINA DISEASE

This application claims priority to U.S. Provisional Patent Application Ser. Nos. 62/330,297 and 62/330,337, filed May 2, 2016, the disclosures of which are incorporated herein by reference in their entireties.

FIELD

This disclosure describes systems and methods for detecting retina disease.

BACKGROUND

Ocular disease is commonplace, especially in people with diabetes. Typically, patients visit an ophthalmologist, retinologist or other eye care professional on a regular basis. During that visit, the eye care professional may observe the patient's retina, such as by looking through the patient's pupil. In some instances, the eye care professional may have automated equipment to photograph the patient's retina.

The eye care professional may then look at the images and mentally compare these to other retinas that they have observed. Abnormalities, such as blood leaks, partial detachment of the macula or retina, or macular degeneration. The eye care professional may also view earlier images taken from the patient's history to determine if there are any changes to the patient's eye.

This examination, while effective at detecting gross abnormalities and large changes, may not be effective in observing small changes to the patient's retina.

Therefore, it would be beneficial if there were an objective method for determining the health of a patient's eye. Further, it would be advantageous if there were a system that could provide this objective test method.

SUMMARY

A system and method for diagnosing retina disease is disclosed. The method comprises capturing a plurality of images of the vascular network within the retina, such as through the use of optical coherence tomography (OCT). This plurality of images are then processed to determine the location and diameter of each vessel in the vascular network in the retina. The vascular network is then divided into a plurality of equal unit volumes. The vessel density, vascular volume density and other metrics can then be determined for each unit volume. This information can then be used to identify retina disease. The information can be parsed and presented in a variety of ways.

BRIEF DESCRIPTION OF THE DRAWINGS

For a better understanding of the present disclosure, reference is made to the accompanying drawings, in which like elements are referenced with like numerals, and in which.

DETAILED DESCRIPTION

There are various methods that can be used to extract vascular networks from a plurality of images. For example, in one embodiment, a filter is used to identify the center of a blood vessel. This filter may assume that the density of the blood vessel is greatest at its centerline, and decreases as one moves away from the center toward the outer edge of the vessel. In one particular embodiment, thin slices of a vessel are created using this filter. These slices may be referred to as disks. A series of disks are linked together to form a three-dimensional structure containing information relating to the local size, shape, branching, and other structural features at any point in the vascular tree.

Some embodiments of a vessel representation that employ these discs are referred to herein as the Poker Chip™ representation due to the similarity to a stack of poker chips. The Poker Chip™ representation treats a vessel as an aggregation of cylindrical cross-sections or discs with continuously varying diameters, wherein each disc in the Poker Chip™ representation is hereinafter referred to simply as a Poker Chip™ or collectively as Poker Chips™. While in theory, the "thickness" of each Poker Chip™ is infinitesimally small, in practice the thickness of each Poker Chip™ may be related to the resolution of the image(s) from which the geometry was extracted. Thus, each Poker Chip™ may have associated geometry including, for example, center location, radius and orientation, as discussed in further detail below.

Figure 1:
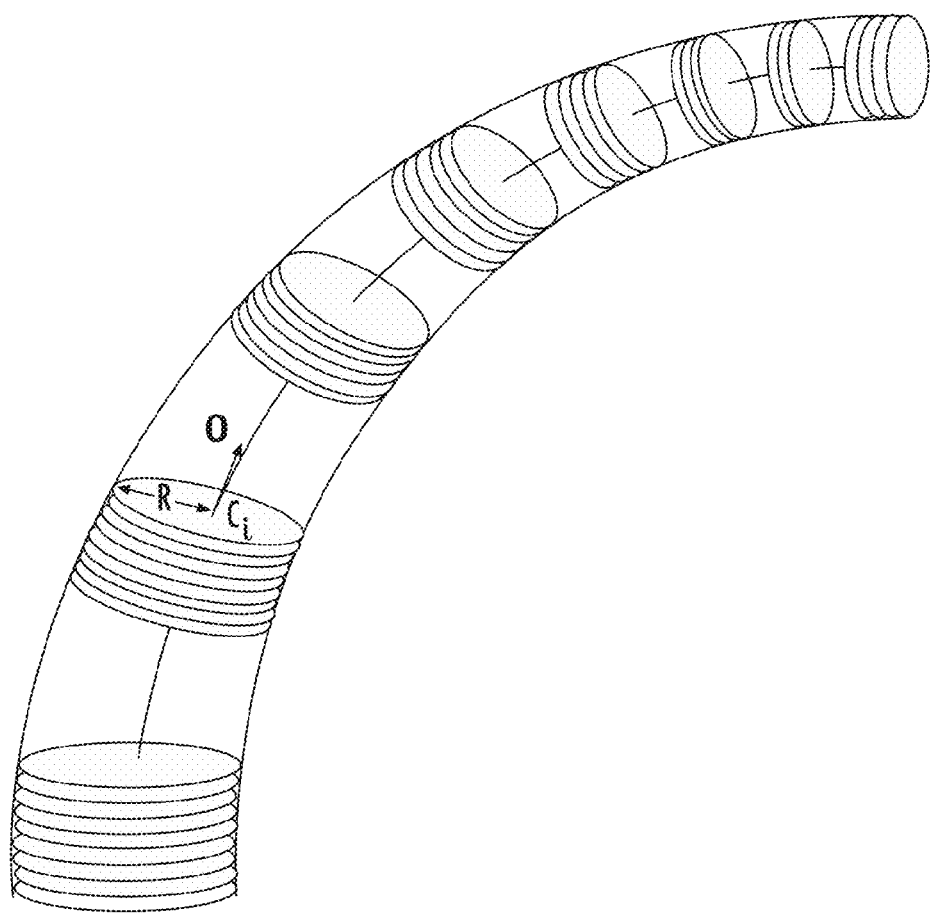
FIG. 1 is a representation of a blood vessel in the present disclosure.

FIG. 1 illustrates a schematic of the Poker Chip™ representation. According to some embodiments, each Poker Chip™ is defined by a center location, a radius and an orientation. The center location $C_i$ represents the center of the vessel, for example, determined by centerline filtering. The radius R represents the radius of the vessel at location $C_i$ and the orientation, O, is the angle of the normal of the Poker Chip™ at location $C_i$, and represents the tangent of the centerline of the vessel at location $C_i$. It should be appreciated that the Poker Chip™ representation may include additional parameters.

To compute some of the higher order information, it may be beneficial to also include in the Poker Chip™ representation information about neighboring Poker Chips™. For example, information about how the Poker Chips™ link together may be valuable in understanding the vessel structure as a whole. Algorithms have been developed that facilitate linking Poker Chips™ together to provide membership information with respect to which Poker Chips™ belong to which vessel and information regarding which Poker Chips™ are adjacent to one another. After linking has been achieved, more sophisticated vessel analysis may be performed.

One system for extracting geometry from images may include a number of processing blocks including: a scale detector, an orientation detector, centerline filtering, non-maximum suppression and linkage. Each of these processing blocks may be a software module or application that is executed on a computer or other processing unit. The processing unit can be implemented in numerous ways, such as with dedicated hardware, or with general purpose hardware, such as personal computers, that is programmed using microcode or software to perform the functions recited herein. A local memory device may contain the instructions, which, when executed by the processing unit, enable the system to perform the functions described herein. This local memory device may be a non-volatile memory, such as a FLASH ROM, an electrically erasable ROM or other suitable devices. In other embodiments, the local memory device may be a volatile memory, such as a RAM or DRAM.

Briefly speaking, the system works as follows: firstly, the scale detection and orientation detection modules may be applied on 3D images to obtain correct size and orientation parameters for centerline detection (e.g., scale and orientation parameters for the centerline filters); secondly, based on the parameters obtained from scale detection and orientation detection modules, the centerline filter may be applied on every voxel of a 3D image, or applied on a subsection of voxels for which centerline detection is desired. The generated response field formed by applying the centerline filter indicates the likelihood that the associated voxel corresponds to the vessel centerline; finally, non-maximum suppression and linkage is applied on the centerline response field to extract the vessel centerline and obtain a vessel mathematical representation (e.g., a linked Poker Chip™ representation). One illustrative example of this system may be found in U.S. Patent Publication 2015/0302584, which is incorporated herein by reference in its entirety. Of course, other methods of extracting vasculature from a set of images may also be used.

As a result of linking the centerline points together, each of which represents a Poker Chip™ having a center location (the centerline point), a radius and a direction of the centerline at the center location, further geometry of the vessel may be computed. Referring back to the schematic of the Poker Chip™ representation in FIG. 1, having computed each of the center location $C_i$, the radius R and the orientation O, and having linked the adjacent Poker Chips™, additional geometry of the blood vessels may be determined. For example, the linked orientation parameters capture information about the geometry of the centerline. For example, by integrating the orientation vectors, the centerline curve may be obtained. That is, because the orientation vectors represent the tangents of the centerline curve at each location $c_i$, the centerline curve may be recovered from linked tangents by integrating over some desired segment of Poker Chips™.

In addition, the linked Poker Chips™ may be used to determine higher order and/or more sophisticated geometrical properties. For example, derivatives of the linked orientation vectors may be used to determine the curvature of the vessel. The centerline curve, length of the curve and curvature parameters may be used to determine various tortuosity parameters, which may be used to characterize the vessels. Moreover, the Poker Chip™ representation carries distribution information with respective to the density of vessel material, the relative distribution of vessels at different radii, etc. These geometrical, structural and distribution parameters may be used in a number of ways to analyze vasculature, as discussed in further detail below.

After the images have been processed to create the Poker Chip™ representation, additional processing may be performed. For example, in one embodiment, the Poker Chip™ representation, which is a three-dimensional computer model where the vasculature is represented by a series of stacked disks or Poker Chips™, can be divided into smaller equal sized volumes. This processing may be performed using a computing device, such as a personal computer or server, having a processor and non-transitory storage medium to store instructions. Those instructions, when executed by the processor, enable the computing device to perform the functions and create the images described herein.

In one particular embodiment, the equal sized volumes may be cubes, where each side of the cube has a length of 200 μm. Of course, the cubes may also have any other dimension. Cubes may be advantageous, since these cubes can be used to fill the entire volume, without any empty space. In some cases, these unit volumes may be referred to as Ice Cubes. Of course, the disclosure is not limited to using cubes as the equal sized volumes. For example, any rectangular prism may be used. Further, other equal sized three-dimensional shapes that can be placed adjacent to one another without any empty space may be used.

The subdivision of the Poker Chip™ representation into a plurality of Ice Cubes allows higher level calculations to be performed. For example, in one embodiment, the number of Poker Chips™ in each Ice Cube can be counted. This metric may be defined as the vascular density per Ice Cube. In another embodiment, the volume of the vasculature may be important. This may be calculated by summing the volumes of all of the Poker Chips™ in each Ice Cube. This can be achieved since each Poker Chip™ includes, as one of its parameters, a radius. This metric may be referred to as Vascular Volume density per Ice Cube.

Either of these two metrics, Vascular Density per Ice Cube and Vascular Volume Density per Ice Cube, may provide an indication of the perfusion of blood within the retina. Further, these metrics may provide objective data regarding the degree of perfusion, enabling detection of potential retina disease and disease progression.

Figure 2:
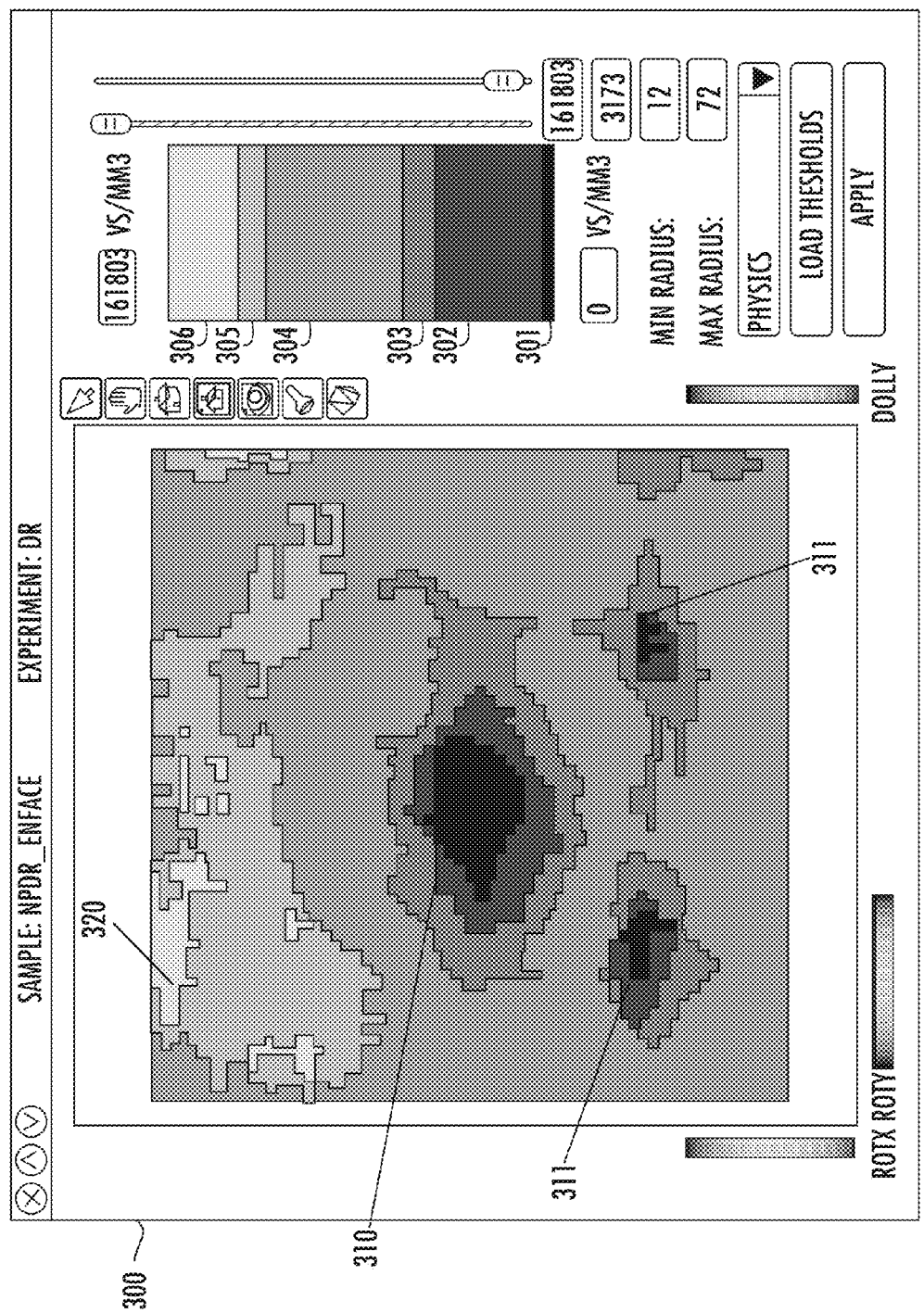
FIG. 2 is a representative graph for a healthy retina.
Figure 3:
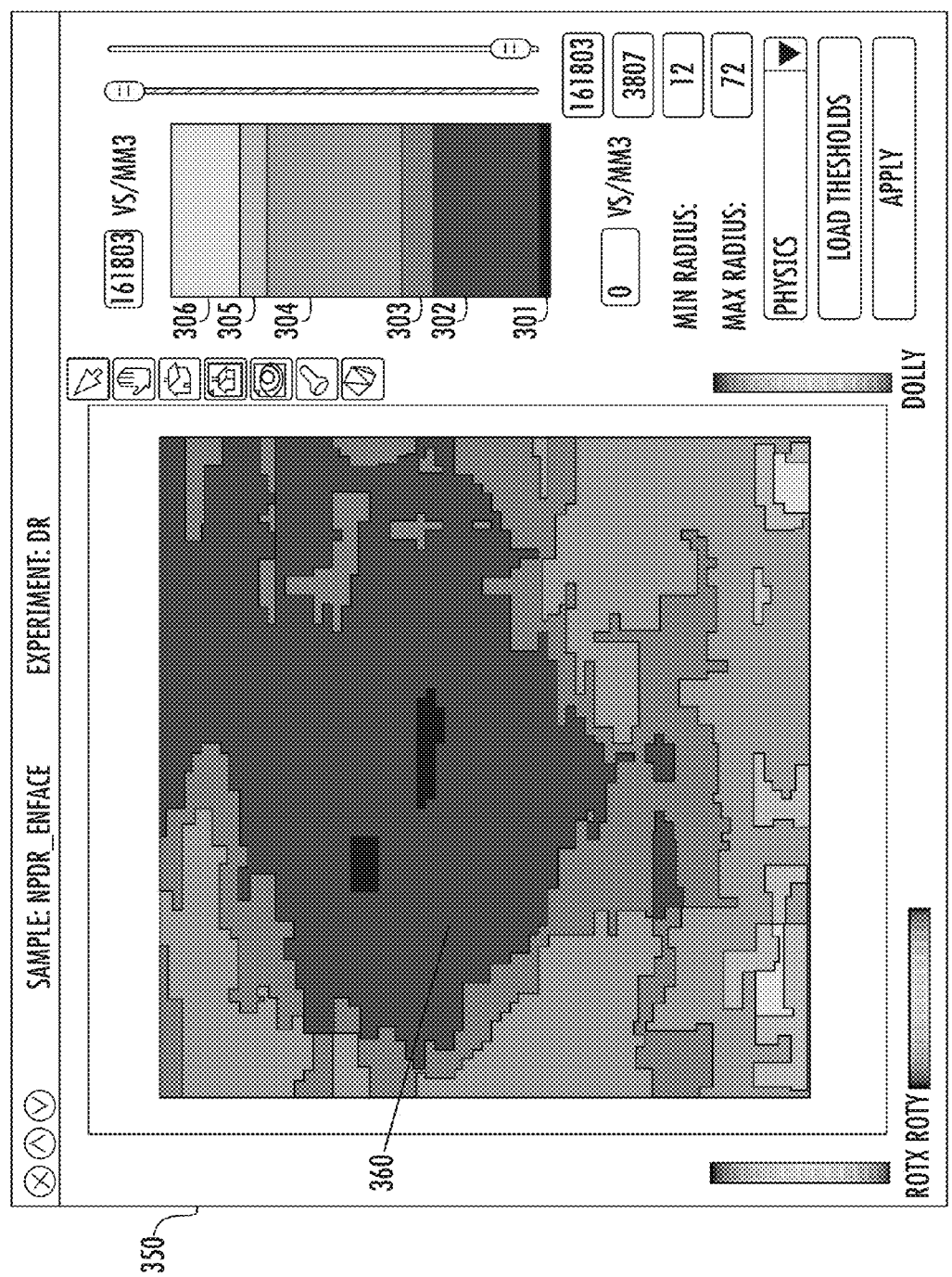
FIG. 3 is a representative graph for a patient with non-proliferative diabetic retinopathy.
Figure 4:
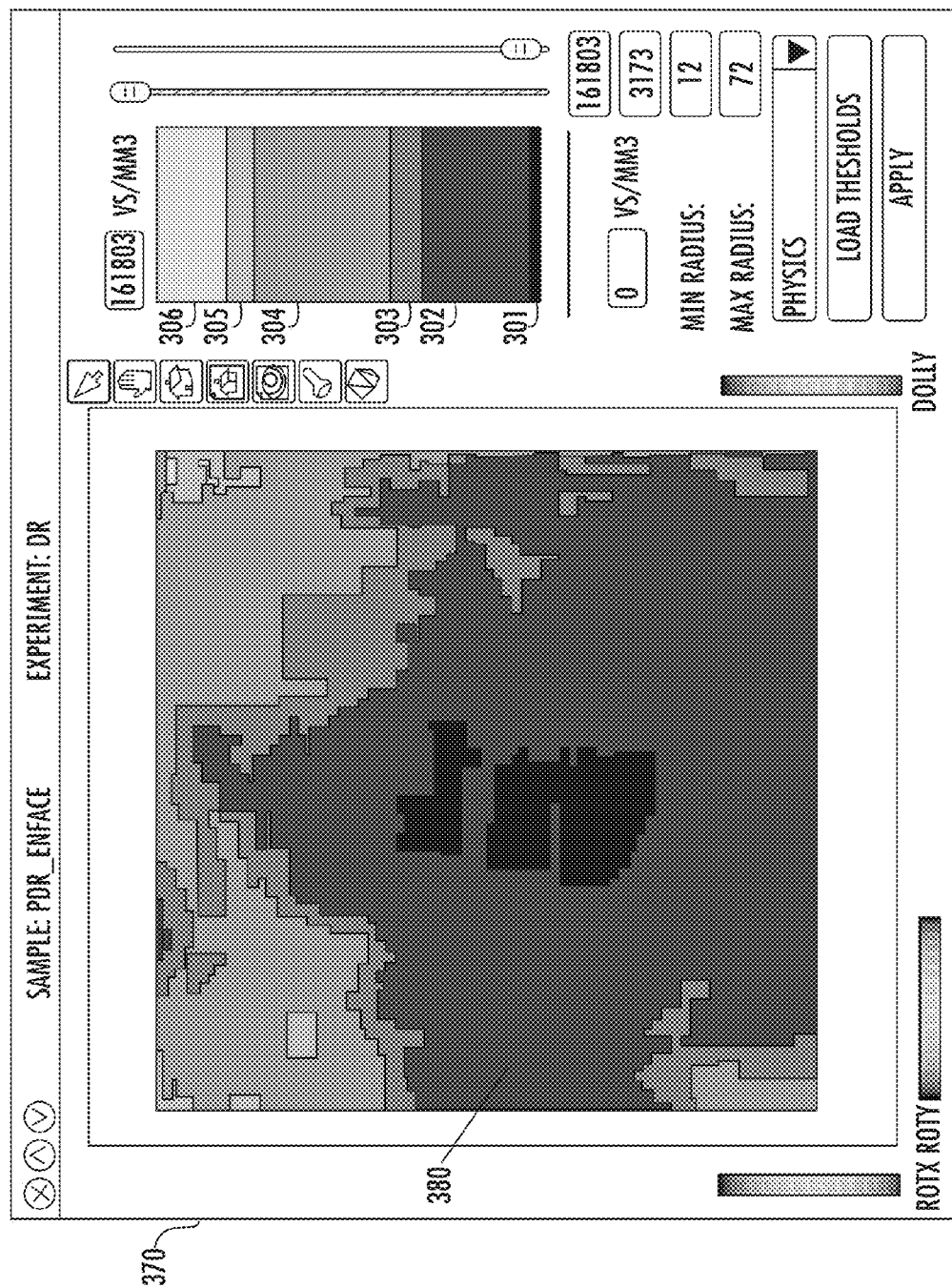
FIG. 4 is a representative graph for a patient with proliferative diabetic retinopathy.

FIGS. 2-4 represent color coded graphs showing the Vascular Density of each Ice Cube in a retina. To improve understanding, the graphs use a range of gray scales. There represent densities from 0 Poker Chips™/cubic millimeter to 161,803 Poker Chips™/cubic millimeter. The darkest shade, identified as 301, is the lowest density. The lightest shade, identified as 306, is the highest density. The remaining shades 302-305, represent ranges of densities between these two extremes. Thus, the darker the shade, the lower the vascular density of that Ice Cube.

As described above, the 3D Poker Chip™ Representation is subdivided into a plurality of Ice Cubes. In other words, assume that the Poker Chip™ Representation is divided into a plurality of Ice Cubes, where there are x Ice Cubes in the X direction, y Ice Cubes in the Y direction and z Ice Cubes in the Z direction, for a total of x*y*z Ice Cubes. In this illustration, Z may represent the depth direction. In this particular embodiment, the Ice Cubes being displayed may all lie in a single plane. In other words, these graphs may show x*y Ice Cubes, where there is only one Ice Cube in the Z direction. This plane may represent a layer or a portion of a layer of the retina. In another embodiment, the graphs may represent more than one Ice Cube in the Z direction. In these embodiments, the graphs may average the vascular density of all Ice Cubes in the Z direction and display that average in the graph. In such an embodiment, these graphs may represent x*y average values. In another embodiment, the graphs may sum the vascular density of all Ice Cubes in the Z direction and display that sum in the graph. In such an embodiment, these graphs may represent x*y summed values While the above description assumes that the graphs display a rectangular area, other embodiments are also possible and the disclosure is not limited to graphs showing x*y Ice Cubes.

FIG. 2 is a representative graph 300 for a healthy retina. FIG. 2 shows a large central area 310 which has a lower vascular density than the surrounding areas. This area consists mostly of Ice Cubes having shades 301, 302. This area may be the macula. Two smaller areas 311 also display lower vascular density than the surrounding regions. Finally, there is a region 320 which displays slightly higher vascular density. Region 320 consists mostly of Ice Cubes having shades 305, 306.

FIG. 3 is a representative graph 350 for a patient with non-proliferative diabetic retinopathy (NPDR). In this figure, the central area 360, which has a lower vascular density (i.e., shades 301, 302) than the surrounding areas, has grown in comparison to FIG. 2. Specifically, the area surrounding the macula has grown outward and also expanded toward the upper right side of the graph.

FIG. 4 is a representative graph 370 for a patient with proliferative diabetic retinopathy (PDR). In this figure, the central area 380, which has a lower vascular density (i.e., shades 301, 302) than the surrounding areas, has grown even larger in comparison to FIG. 2.

FIGS. 2-4 provide a visual indication of the change in vascular density due to the progression of diabetic retinopathy. It is clear from these graphs that, in each successive graph, the amount of the retina with a low vascular density (i.e., shades 301, 302) increases.

Figure 5:
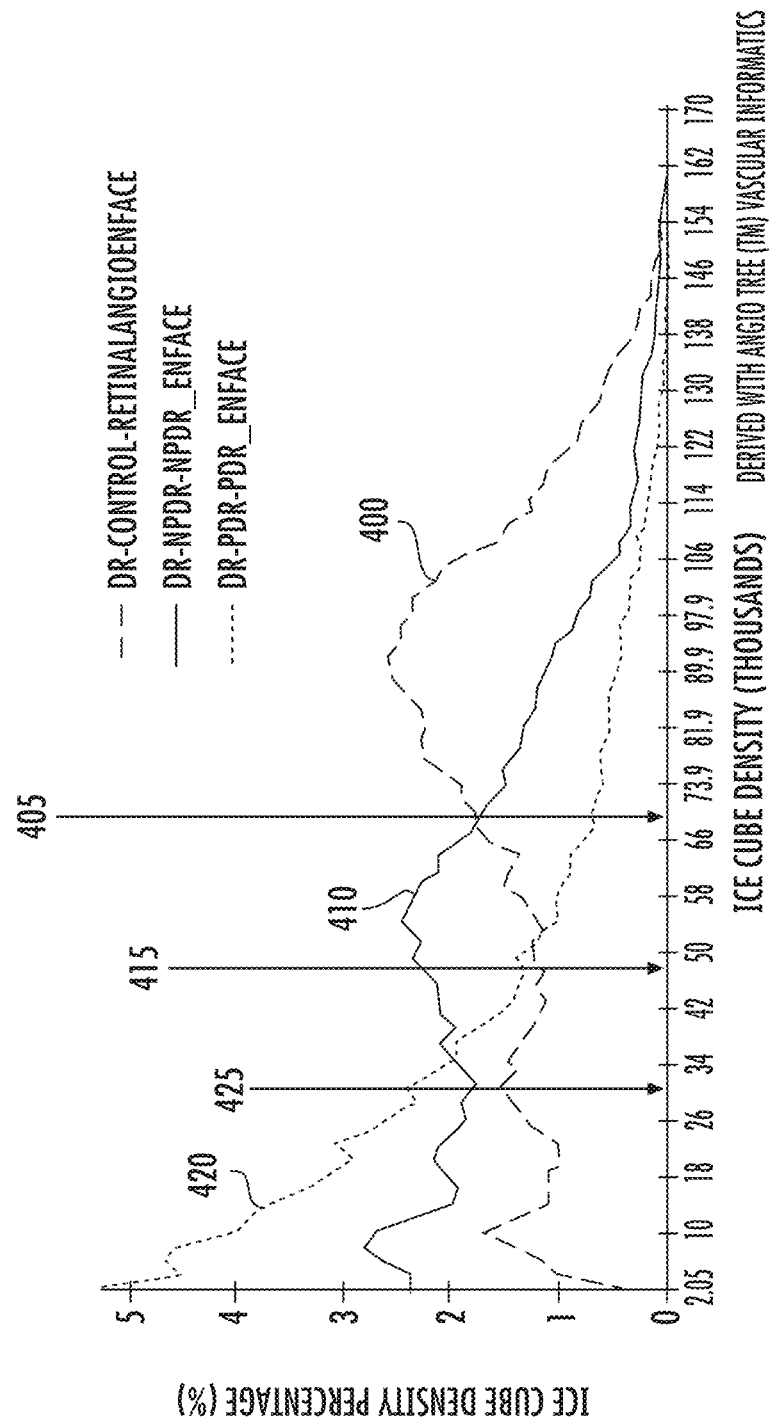
FIG. 5 shows a histogram of vascular density and mean values.

FIG. 5 shows the data from FIGS. 2-4 in a different format. In this graph, a histogram is presented. The horizontal axis represents the vascular density, as measured in thousands of Poker Chips™ per cubic millimeter. In this particular embodiment, the vascular density per Ice Cube has been separated into 80 bins, although any number may be employed. The vertical axis represents the percentage of Ice Cubes having a particular vascular density. Line 400 represents the histogram for the healthy retina of FIG. 2. In this histogram, the density distribution is roughly uniform until about 65,000 Poker Chips™ per cubic millimeter. At this point, there is a slight increase in density distribution until about 105,000 Poker Chips™ per cubic millimeter. The density distribution steadily decreases to about 150,000 Poker Chips™ per cubic millimeter. Further, line 400 resembles a bell curve, especially at density values greater than about 40,000 Poker Chips™/cubic millimeter. Line 410 represents the histogram for the patient with NPDR of FIG. 3. Note that line 410 has a much higher percentage of Ice Cubes having low vascular densities. In fact, Line 410 shows that the patient with NPDR has a greater percentage of Ice Cubes with vascular densities less than 72,000 Poker Chips™/cubic millimeter than the healthy retina. After this value, the density distribution decrease quickly. Thus, line 410 has a region of roughly constant values, followed by a region of steadily decreasing values. Line 420 represents the histogram for the patient with PDR of FIG. 4. Note that line 420 has a much higher percentage of Ice Cubes having low vascular densities. In fact, Line 420 shows that the patient with PDR has a greater percentage of Ice Cubes with vascular densities less than 53,000 Poker Chips™/cubic millimeter than the healthy retina. Further, line 420 approximates a 1/x function with steadily decreasing values as density increases. In addition to the dramatically differently shaped histograms, the mean vascular density is also very different for each line. Line 405 shows the mean vascular density of a healthy retina, which is about 72,000 Poker Chips™/cubic millimeter. Line 415 shows the mean vascular density of a patient with NPDR, which is about 49,000 Poker Chips™/cubic millimeter. Note that this is nearly 33% less than the mean value for the healthy retina. Line 425 shows the mean vascular density of a patient with PDR, which is about 29,000 Poker Chips™/cubic millimeter. Note that this is nearly 60% less than the mean value for the healthy retina.

The data that is collected by using Poker Chips™ and Ice Cubes may be used in a number of ways.

First, as shown in FIGS. 2-4, the vascular density of each Ice Cube can be plotted on a two dimensional graph. Color coding or shading may then be used to accentuate areas with low vascular density or high vascular density. The area of the low vascular density regions can then be approximated and used to determine whether a patient has or is developing PDR. For example, a predetermined threshold for an acceptable area for the low vascular density regions may be generated. If the area of the low vascular density regions is less than this predetermined threshold, the retina is determined to be healthy. In a further embodiment, a second threshold may be set to distinguish between NPDR and PDR. If the area of the low vascular density regions is less than the first threshold, the retina is determined to be healthy. If the area is between the first threshold and the second threshold, the retina is determined to have NPDR. If the area is greater than the second threshold, the retina is determined to have PDR. In another embodiment, the general shape and/or size of the low vascular density area can be used to make this determination.

Secondly, the vascular density per Ice Cube may be plotted using a histogram. The general shape of the histogram may be used to make a determination whether a patient has or is developing PDR. For example, a histogram that approximates a 1/x function may be determined to represent PDR, while a histogram that is relatively constant and starts decreasing at a value of about 56,000 Poker Chips™/cubic millimeter may be indicative of NPDR. A curve that approximates a bell curve may be indicative of a healthy retina. In other embodiments, the area under the curve may be used to make this determination. For example, if the areas under lines 400, 410, 420 is calculated from 0 to about 35,000 Poker Chips™/cubic millimeter, it is clear that line 420 yields the greatest area, while line 400 yields the lowest area. Similarly, if the area under lines 400, 410, 420 is calculated from 70,000 to 170,000 Poker Chips™/cubic millimeter, it is clear that line 420 yields the lowest area, while line 400 yields the greatest area. Predetermined values for the areas under these curves may be established to distinguish between healthy retinas and those with NPDR and PDR.

Third, the mean value of vascular density per Ice Cube may be used to make a determination about the health of the retina. A first predetermined threshold may be used to distinguish between healthy retinas and other retinas. A second predetermined threshold, lower than the first threshold, may be used to distinguish between NPDR and PDR. For example, referring to FIG. 5, the first predetermined threshold may be a value between line 405 and line 415, while the second predetermined threshold may be a value between line 415 and line 425. In other words, the mean vascular density per Ice Cube for a patient may be determined. Once determined, that mean vascular density per Ice Cube can be compared to the first and second predetermined threshold to determine the state of the patient's retina.

Figure 6:
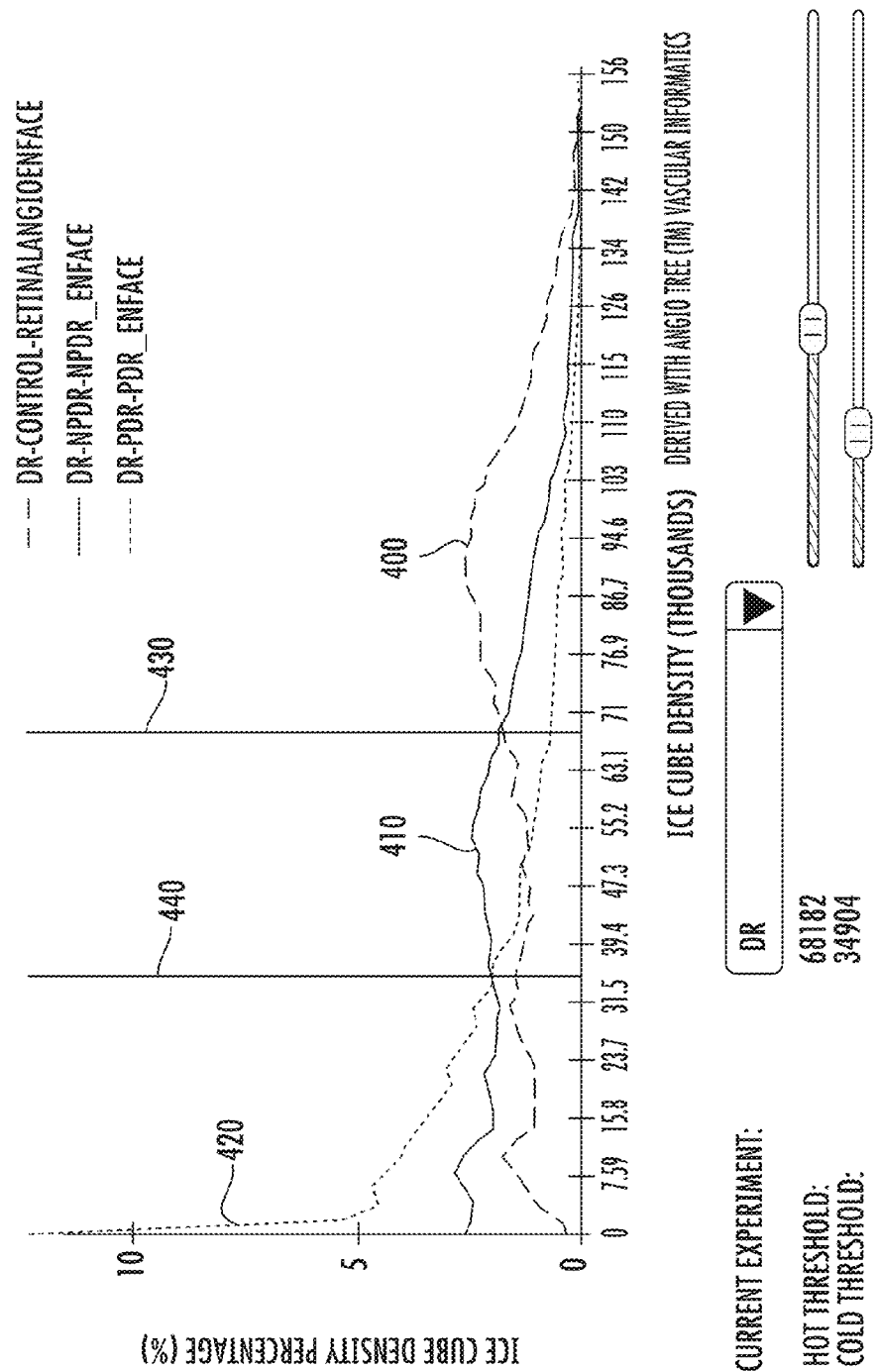
FIG. 6 shows the histogram of FIG. 5 with two thresholds to define hot and cold regions.

The two threshold values described above can be utilized in other ways as well. FIG. 6 shows the histogram of FIG. 5 with two threshold values included. The first threshold value 430 has a higher value than the second threshold value 440. In some embodiments, these threshold values may be chosen based on empirical data concerning mean values for the three retinas. In other embodiments, these threshold values may be chosen based on the shape of the histograms. For example, the second threshold value 440 may be chosen as the value at which line 420 crosses line 410. Similarly, the first threshold value 430 may be chosen as the value at which the line 410 crosses line 400. In this particular figure, first threshold value 430 is set to 68,182 Poker Chips™/cubic millimeter, while the second threshold value 440 is set to 34,904 Poker Chips™/cubic millimeter.

Figure 7:
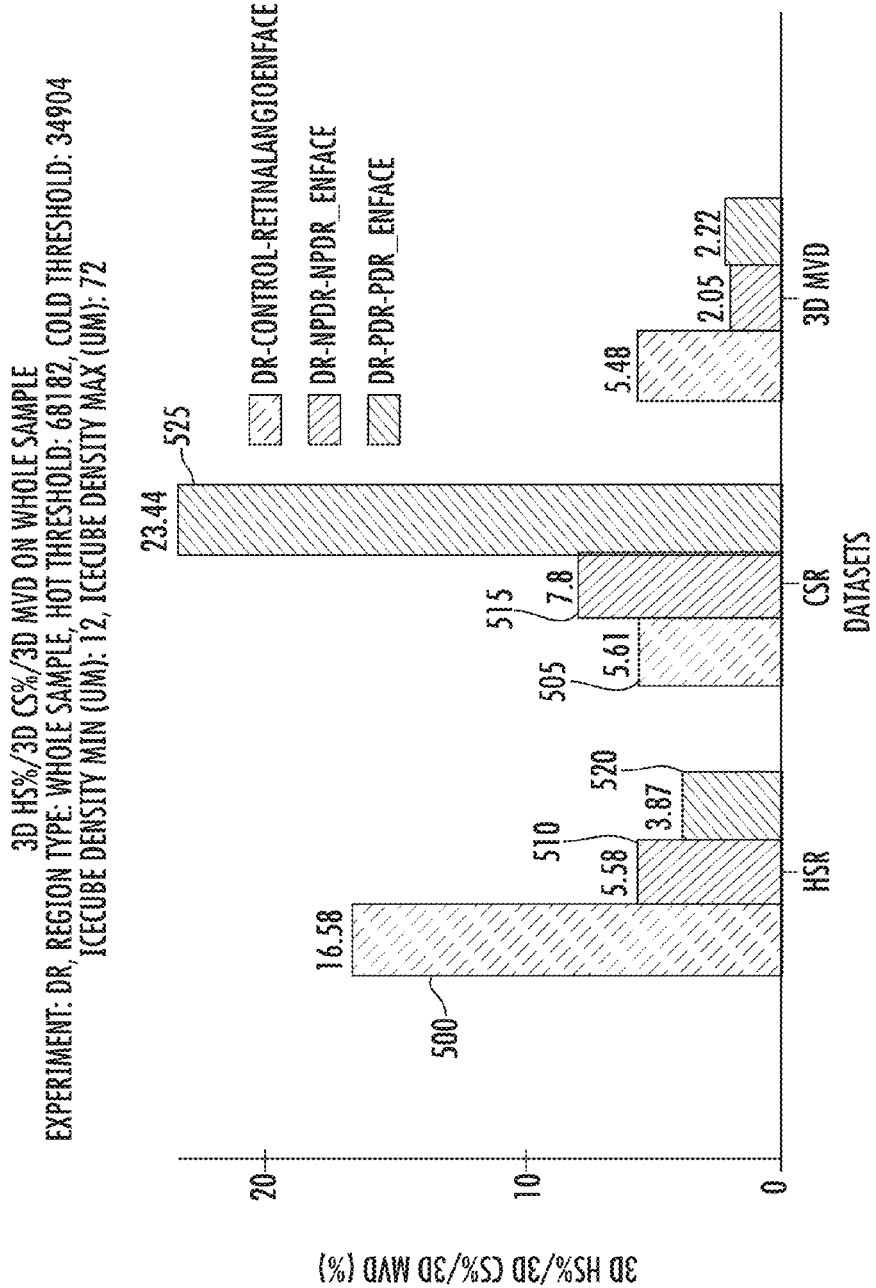
FIG. 7 shows the percentage of hot and cold regions for three representative retinas.

These two threshold values 430, 440 may be used to define three different regions. Ice Cubes having a vascular density less than second threshold value 440 may be referred to as cold regions, while Ice Cubes having a vascular density greater than the first threshold 430 may be referred to as hot regions. The Ice Cubes having values between the first threshold value 430 and the second threshold value 440 may be referred to as normal regions. The percentage of Ice Cubes that fall into each region may then be calculated. FIG. 7 shows a graph illustrating this data. Bar graph 500 shows that 16.58% of the Ice Cubes in the healthy retina of FIG. 2 are in the hot region. In contrast, bar graph 510 shows that only 5.58% of the Ice Cubes in the NPDR retina are in the hot region. Bar graph 520 shows that only 3.87% of the Ice Cubes in the PDR retina are in the hot region. In contrast, bar graph 505 shows that only 5.61% of the Ice Cubes in the healthy retina are in the cold region. Bar graph 515 shows that 7.8% of the Ice Cubes in the NPDR retina are in the cold region. Bar graph 525 shows that 23.44% of the Ice Cubes in the PDR retina are in the cold region. These values can be used in a variety of ways.

First, the absolute percentages of hot regions and/or cold regions may be used to determine the status of the retina. For example, a healthy retina may have less than 6% of the Ice Cubes in the cold region and more than 15% of the Ice Cubes in the hot region. A retina with PDR may have more than 20% in the cold region and less than 4% in the hot region. A retina with NPDR would have values between those of healthy and PDR retinas. Of course, the percentages stated above may be adjusted as needed. Further, the determination may be made using only one set of percentages; either the hot region percentage or the cold region percentage.

Second, the ratio of hot region to cold region may be used to make a determination. The ratio for a healthy retina is 16.58/5.61, or 2.95. The ratio for NPDR and PDR retinas are 0.71 and 0.17, respectively. Thus, threshold values may be used to distinguish between healthy retinas and diseased retinas based on the ratio of hot regions to cold regions.

Figure 8:
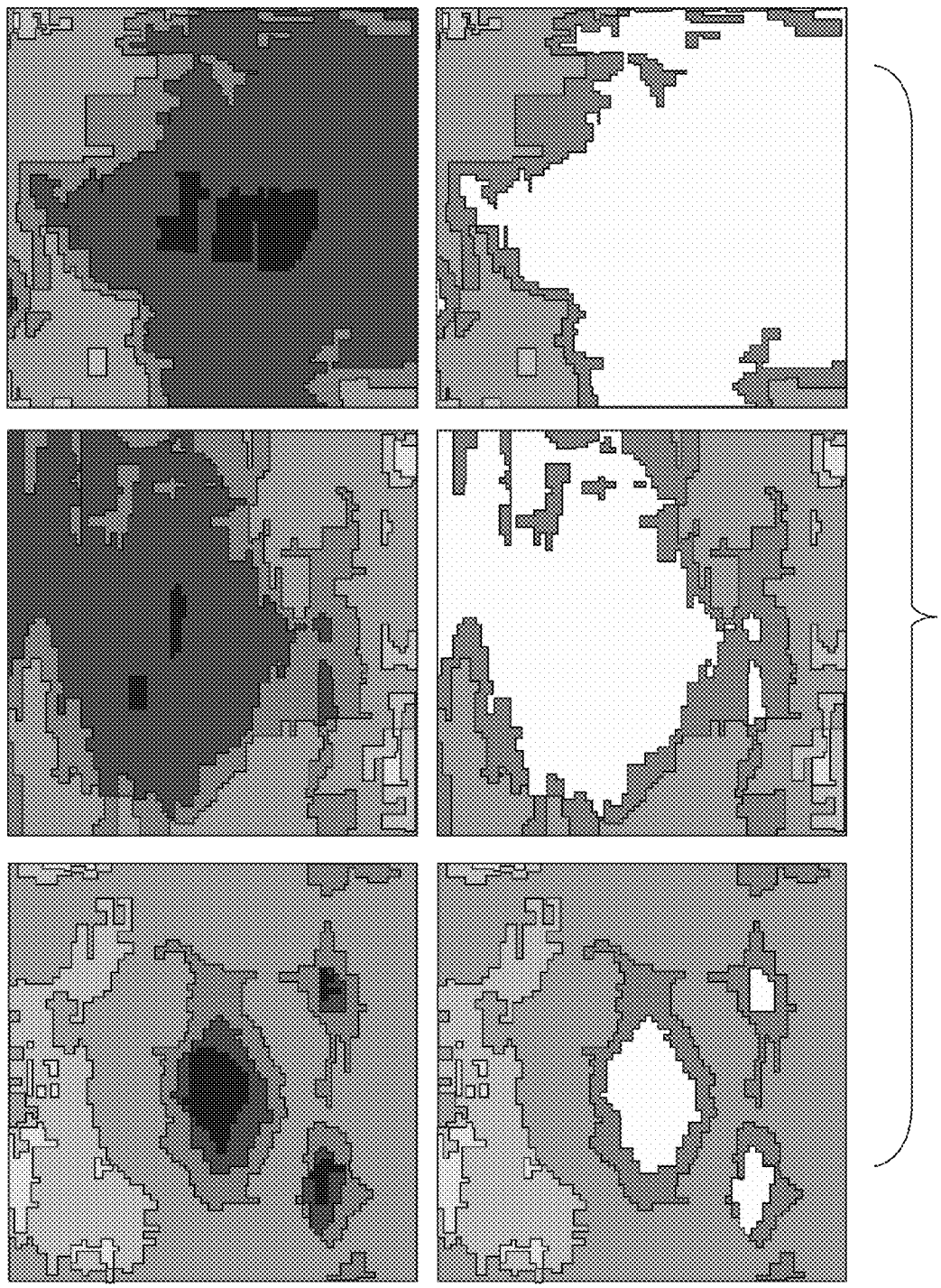
FIG. 8 shows the graphs of FIGS. 2-4 and those graphs highlighting only the hot regions.

FIG. 8 shows the location and shape of the hot regions in the color coded graphs. The top row of graphs in FIG. 8 represent FIGS. 2-4, respectively. The lower row of graphs show the same graphs with only the hot regions shown. In other words, areas with shades 301, 302 have been removed in the lower row of graphs.

FIG. 6 shows the use of a first threshold value 430 and a second threshold value 440 to define three regions (hot, cold and normal). However, in certain embodiments, only the first threshold value 430 is used. This first threshold value 430 is used to distinguish between the hot region and all other regions. Thus, in certain embodiments, rather than calculating hot and cold region percentages, as shown in FIG. 7, only hot region percentages are calculated.

Figure 9:
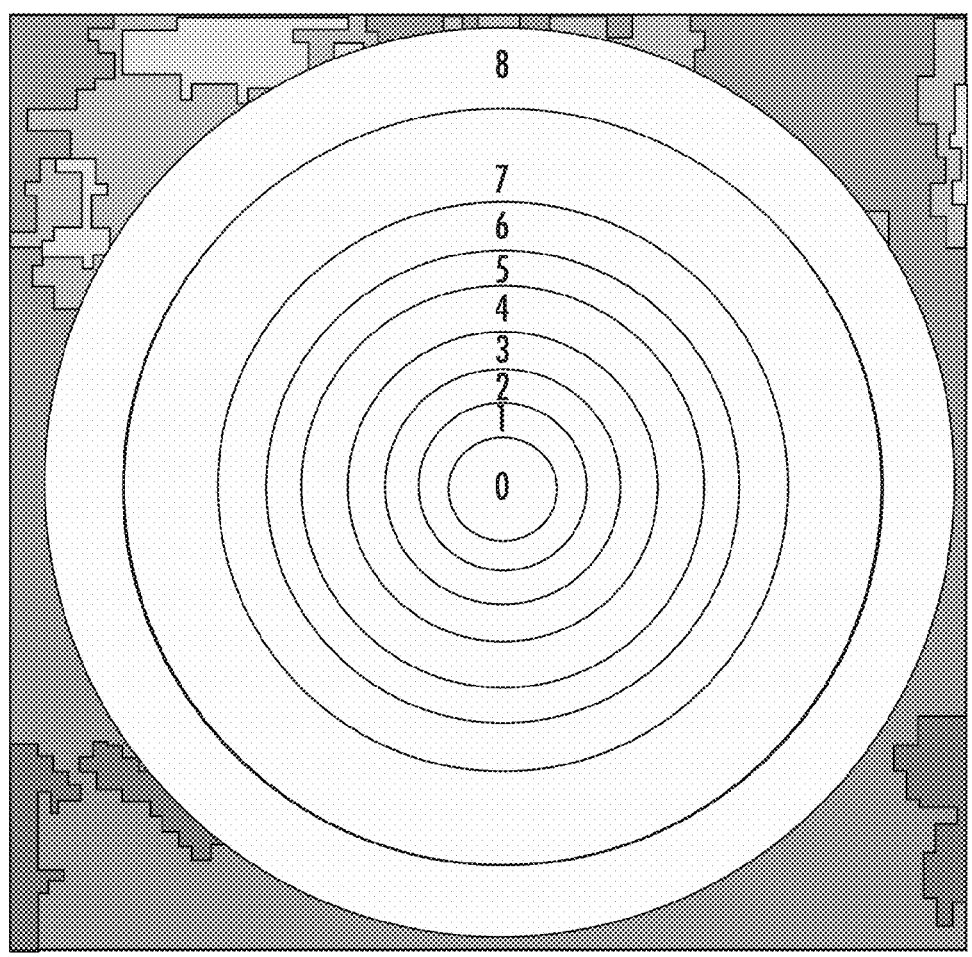
FIG. 9 shows a method of segmenting the retina into smaller parts.

Furthermore, the graphs of FIGS. 2-4 may be segmented in different ways. For example, as shown in FIG. 9, the retina may be segmented into a plurality of rings. These rings may be concentric, but do not need to be so. In one embodiment, each ring is located a predetermined distance from the center of the macula. Rather than compiling data for the entire retina, in some embodiments, it may be beneficial to analyze only a portion of the retina. In one embodiment, the macula is defined as the inner most region 0. One or more annular rings are then constructed around inner most region 0. These annular rings also define concentric shells, which are a union of all of the inner rings of smaller radius. Referring to FIG. 9, shell 6 may comprise the annular rings 1-6. Shell 6 may or may not also include the inner most region 0. In certain embodiments, the onset of NPDR may be detected earlier by looking only at one or more of the annular rings or at the concentric shells formed by these rings. For example, in comparing FIG. 2 to FIG. 3, note that the most dramatic change is the decrease in vascular density extending outward from the macula. By looking at the metrics described above for only a portion of the retina, such as specific annular rings or shells, earlier detection may be possible. In one embodiment, the techniques described above are used in conjunction with, for example, rings 1-6. By ignoring data in the outermost regions, differences in the vasculature of the retina may be more pronounced. Of course, data from any ring or combination of rings may be used to make these determinations. The use of rings and shells is one method for narrowing the retina location where vascular changes due to disease are observed. This technique enables determining the extent of the disease as a function of its radius from the center of the macula.

For example, the use of rings and shells allows certain analysis that might not be otherwise possible. For example, by performing the analysis and producing a histogram for each shell or ring, an eye care professional may determine (and plot) the mean vascular density for each ring or shell. This information may reveal information about retina disease. As with all embodiments, this analysis may be made for a single layer of the retina or for multiple layers.

Further, the inner most region 0, which represents the macula, can be further analyzed to determine vascular density of vessels of all diameters, or for vessels of only a specific range of diameters. For example, the vascular densities of capillaries, having a diameter of less than 15 micrometers or less than 10 micrometers may be determined.

Further, the vascular morphology of the macula can be analyzed. First, the macula is identified, such as by isolating the innermost circle of lowest vascular density. Then, other parameters of interest can be analyzed. This includes the formation of neo-vasculature, which is curvy and tortuous and features a disorganized collection of branching points.

Figure 10:
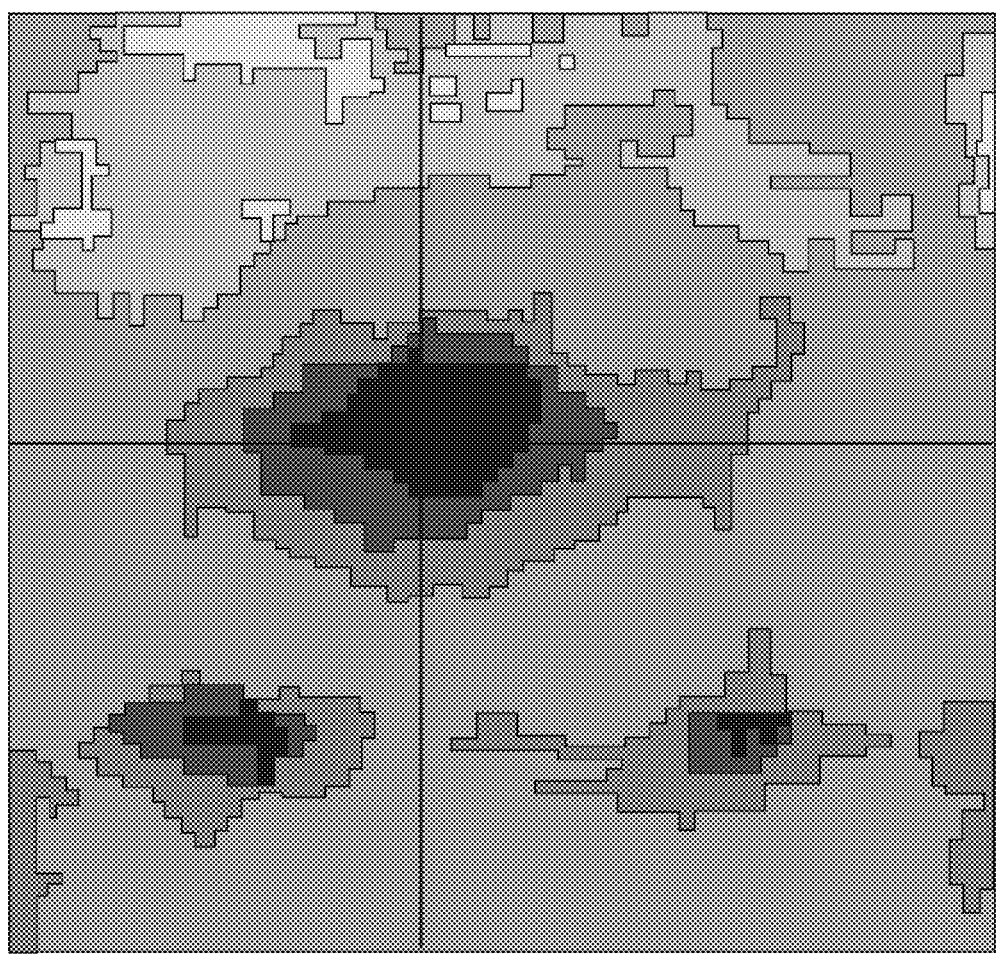
FIG. 10 shows a second method of segmenting the retina into smaller regions.

FIG. 10 shows a different method of segmenting the graphs of FIGS. 2-4. In this embodiment, the retina is divided into four quadrants. These quadrants may be defined using the macula as the origin, such that the two perpendicular lines that define the four quadrants pass through the center of the macula. In other embodiments, the center of the retina may be used as the origin. In comparing FIGS. 2 and 3, it can be seen that the upper right quadrant may be most affected by the NPDR. Thus, by looking at the metrics described above for only one or more quadrants of the retina, earlier detection may be possible.

Figure 11:
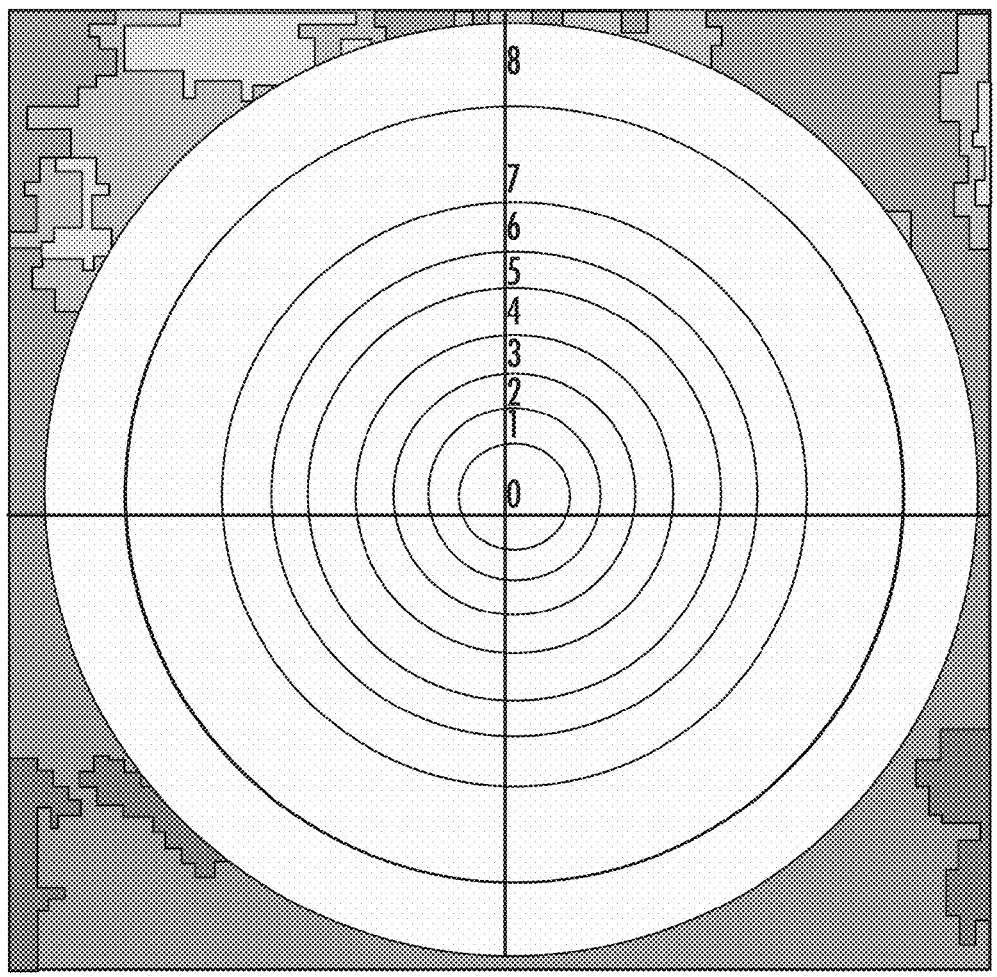
FIG. 11 shows the methods of FIG. 9 and FIG. 10 combined.

Further, as shown in FIG. 11, the segmentation of the retina using rings and shells, as shown in FIG. 9, can be used in conjunction with the quadrant approach of FIG. 10. In other words, a region of interest may be defined using the ring or shell number or numbers, in combination with the quadrant. For example, the use of rings 1-6 in the upper right quadrant may show the most dramatic change between FIG. 2 and FIG. 3.

Figure 12:
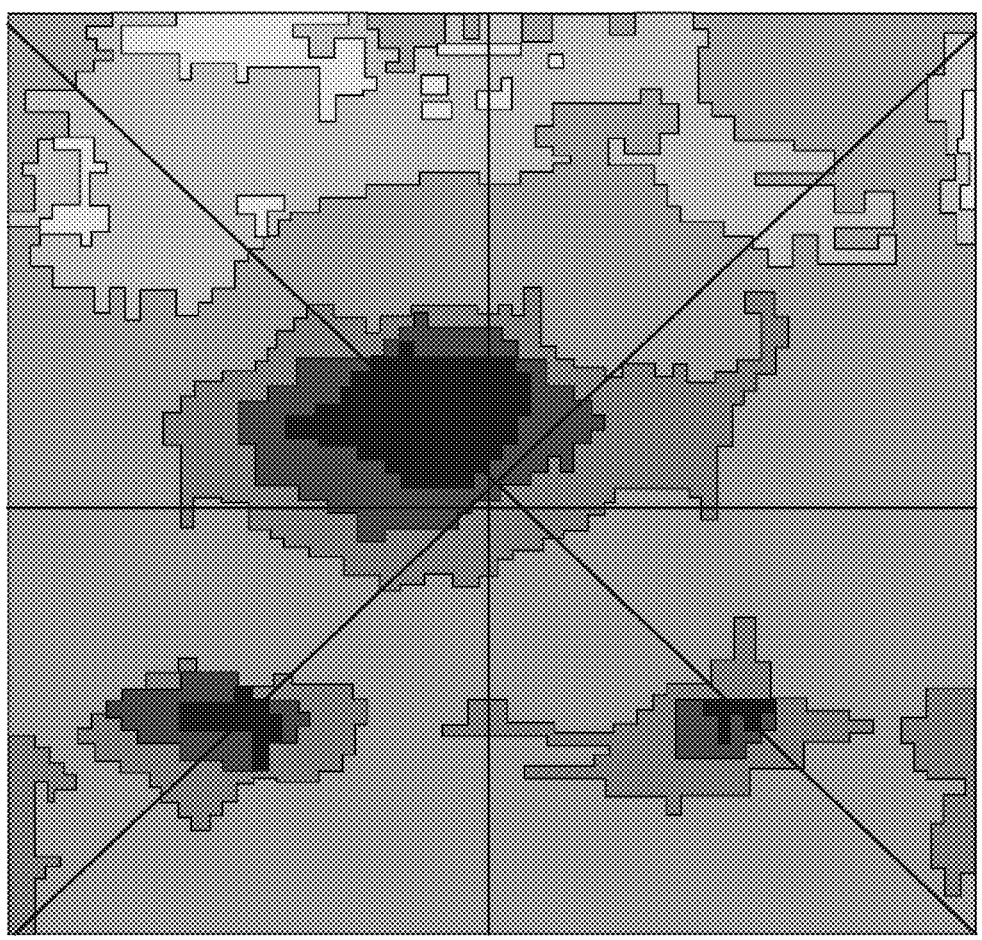
FIG. 12 shows a third method of segmenting the retina into smaller regions.
Figure 13:
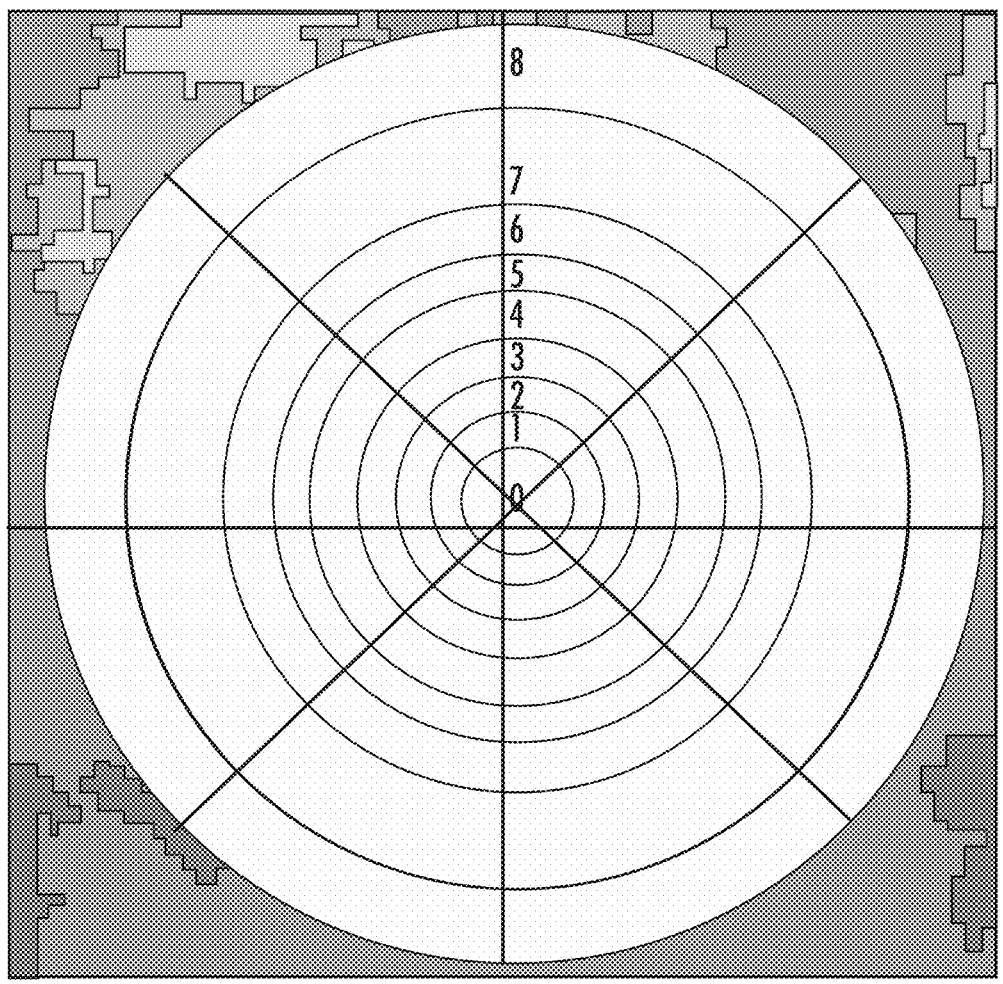
FIG. 13 shows the methods of FIG. 9 and FIG. 12 combined.

Furthermore, the segmentation need not be quadrants. FIG. 12 shows the creation of eight wedges, each of which may have an equal interior angle. In certain embodiments, the wedges are created by pairs of orthogonal lines that meet at the center or near the center of the retina, where each pair of orthogonal lines is rotated with respect to each other pair. In certain embodiments, the pairs of orthogonal lines may not meet at a single point. The disclosure is not limited to only 4 or 8 wedges. Rather, the retina may be divided into an arbitrary number of wedges. In addition, these wedges may be used alone or in combination with the rings shown in FIG. 9. This is shown in FIG. 13.

In yet another embodiment, the quadrants shown in FIG. 10 can be further subdivided by using a plurality of orthogonal intersecting lines, forming a grid. For example, rather than forming 4 quadrants, the plurality of orthogonal lines may be used to create a grid having, for instances, 10×10 grid boxes. Of course, the grid may have any dimensions and need not be equal in the X and Y dimensions.

The above described methods can be applied in a variety of ways. First, the region of interest may be selected. The previous description shows methods of subdividing the retina into rings, shells, wedges and grid boxes. The analysis may be performed on any ring, combination of rings, shell, combination of shells, wedge, combination of wedges, grid box, combination of grid boxes or any combination of rings, shells, wedges and grid boxes. For example, a histogram, with a calculation of mean vascular density, may be performed for only a particular region of interest, such as a subset of the annular rings.

Further, as stated with respect to FIGS. 2-4, the graphs may be created based on a single retina layer. In other embodiments, the graphs may be constructed using a plurality of layers. These different layers may be evaluated separately, such as by creating separate graphs for each layer. In another embodiment, the data for that different layers may be combined, such as by averaging or summing the Poker Chips™.

Additionally, the graphs of FIGS. 2-4 included Poker Chips™ of all diameters. However, other embodiments are also possible. For example, after creating the Poker Chip™ representation, the data may be further filtered to only include Poker Chips™ having a predetermined range of diameters. In another embodiment, the data may be filtered to include Poker Chips™ having one of multiple ranges of diameters. In other words, if the existence of small diameter vessels is indicative of a healthy retina (or a diseased retina), the data presented above can be filtered to only include vessels within the diameter range of interest. For example, the data may be filtered to only include vessels having a diameter of 15 micrometers or less. In another embodiment, only vessels having a diameter of less than 10 micrometers are analyzed.

While the above disclosure describes the graphs as showing either Vascular Density or Vascular Volume Density, other parameters may also be used. For example, in one embodiment, rather than using the number of Poker Chips™ per Ice Cube, the data may be processed to provide other parameters, such as average vessel diameter, average curvature, average length, orientation, tortuosity, and branching density. In other words, any geometric and/or morphological vascular change in the retina as a whole or on specific layer or group of retina layers at certain distances from the macula or from the periphery, could be detected through changes in Ice Cube content density. The above description discloses using the density of Poker Chips™ per Ice Cube (of all diameters or specific diameters or ranges). However, these changes could also be detected by replacing Poker Chips™ with Branching Points Density or with Specific Vessel Branch Geometry Density-straight, curvy, or tortuous branches.

Furthermore, the above description discloses the comparison of a patient's data to a set of predetermined thresholds or other empirical data. Specially, the first and second thresholds 430, 440 shown in FIG. 6 may be based on empirical data. However, other embodiments are also possible.

For example, one can establish retina disease tracking and thresholds by monitoring the retina over time as described in more detail below.

In this embodiment, the health of a patient's retina may be monitored over time, and compared to earlier collected data for the same patient. For example, graphs of vascular density (FIG. 2), vascular density histograms (FIG. 5), mean vascular density (FIG. 5), and percentage of hot and cold regions (FIG. 7) may be compared to like data for the same patient collected at an earlier date. In this way, changes in the mean vascular density can be tracked. Further, changes in hot and cold regions can be tracked. In fact, any parameter that was described above as being compared to a threshold may be compared to an earlier sample to show the degradation of the retina in a particular patient. In this way, the progression of a disease, such as proliferative diabetic retinopathy, may be monitored. Based on these results, the eye care professional may suggest a course of treatment.

For example, the mean value of the vascular density can be monitored, so that decreases in its value can be detected. This may be used to trigger intervention when the value goes down by a predetermined amount, such as 20%. In another embodiment, the certain rings, shells, wedges and/or grid boxes may be monitored so that a gradual lowering of the vascular density in these certain regions is detected. Intervention may be triggered when the vascular density drops below a certain value/threshold. In addition, progression of the lower vascular density into other shells, rings or wedges may also be used to trigger intervention.

This intervention may include any of the following. First, the eye care professional may perform a more detailed examination to further validate the specific retina pathology. Second, the eye care professional may prescribe a treatment regimen, which may include a certain drug compound given at a certain dose, or, a combination of drug compounds, each compound in the combination prescribed at a certain dose.

Further, the eye care professional may create subsequent histograms and compare these to earlier histograms. This information may allow the eye care professional to detect and quantify the response to therapy (either single compound or compounds combination). The eye care professional may also use the comparison of histograms to optimize the response to therapy by changing the initial single compound to another therapeutic compound, changing the dose of the initial single therapeutic compound, modifying the compounds combination in terms of compounds in the combination, dosages of the compounds in the combination, or both of the above.

In summary, the shape, height, and x-axis location of the histogram curve and the mean value of the vascular density per Ice Cube, taken across the full retina or on specific layers or groups of layers, can provide the degree of retina health, including the degree of healthy aging, as well as become the leading indicator on emergence of disease. As a result, the histogram of FIG. 5, if taken on a yearly basis, could become a mass population screening or more specific, for populations predisposed to certain retina of physiological diseases detectable in the retina (e.g. AD, Stroke, CVD, etc.)

Figure 14B:
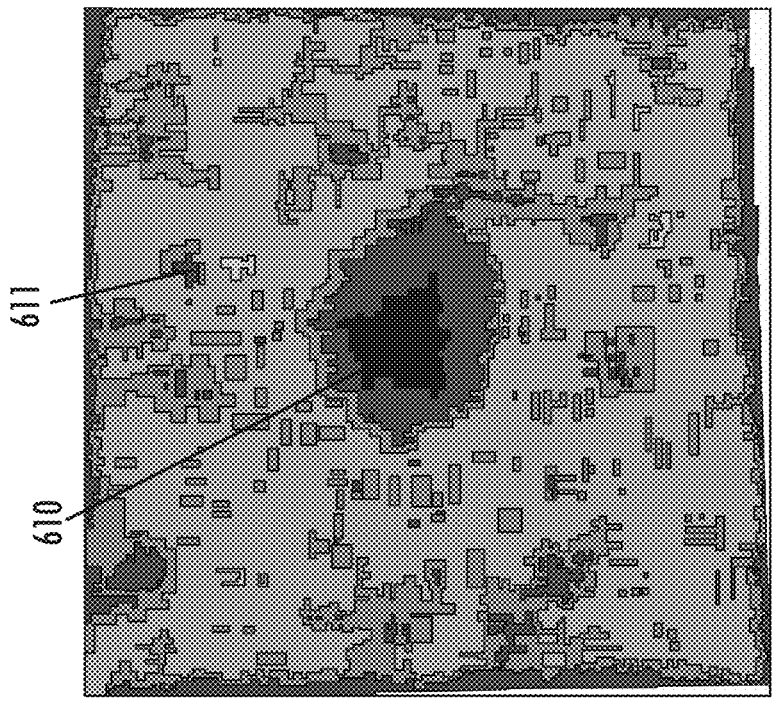
FIG. 14A-14B show representative graphs for a 27 year old patient and a 70 year old patient, respectively.
Figure 14A:
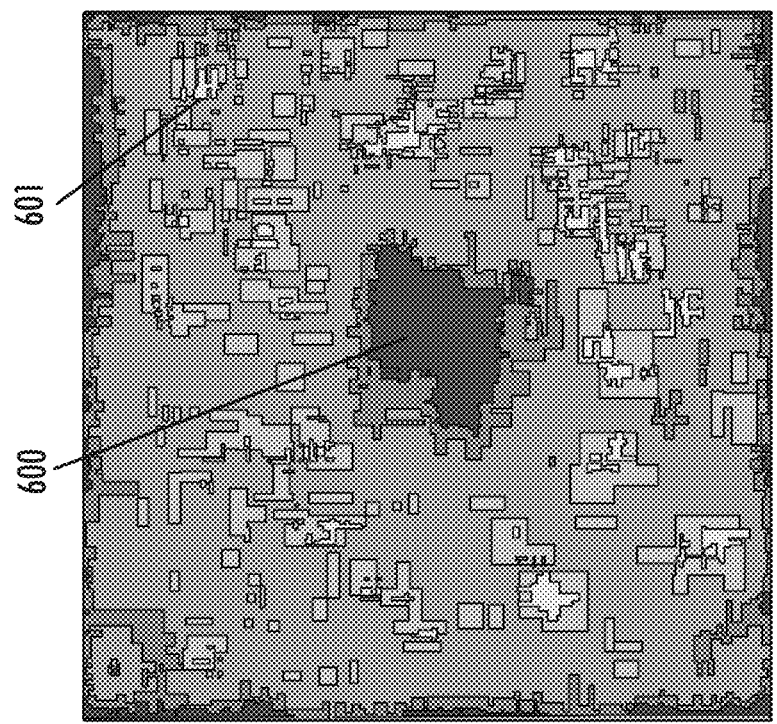

Interestingly, the profile of a healthy retina may change as the patient ages. For example, a young person may have a greater mean vascular density than a healthy older person. FIG. 14A shows a color coded graph of the vascular density of a healthy 27 year old patient. The shading is as described with respect to FIGS. 2-4. Note that the low density central region 600 is relatively small. Further, several areas of high density 601 surround the macula. FIG. 14B is a color coded graph of the vascular density of a healthy 70 year old patient. Note that the low density central region 610 is larger than the central area 600 in FIG. 14A. Further, several areas of low density 611 surround the macula. In certain embodiments, the size of fovea and macula increase with age. By looking at the vascular density per Ice Cube over time, an eye care professional may track the increasing diameter of the fovea and/or macula. The eye care professional can then determine whether this increase in diameter is a result of healthy aging or disease. As with all other analysis described herein, the analysis can be performed for one or more layers of the retina.

Figure 15:
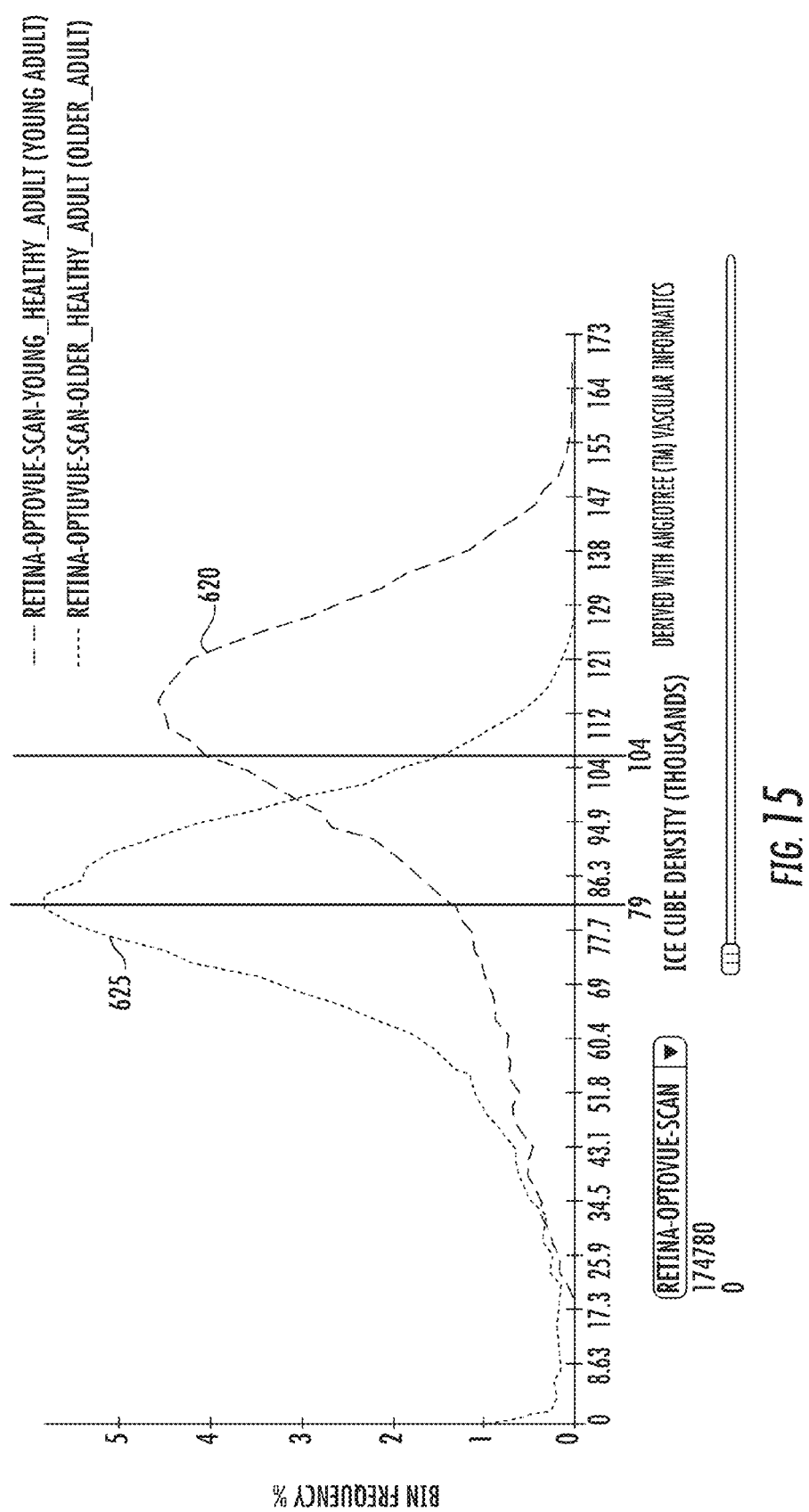
FIG. 15 shows a histogram of vascular density and mean values.

FIG. 15 shows a histogram, similar to that shown in FIG. 5. Line 620 represents the data for the 27 year old patient, while line 625 represents the data for the 70 year old patient. Note that both lines 620, 625 have the same shape, which is approximately a bell curve. However, the most dramatic difference is the center of each bell curve and the mean values. The mean vascular density for the 27 year old patient is about 104,000 Poker Chips™/cubic millimeter, while the mean vascular density for the 70 year old patient is about 79,000 Poker Chips™/cubic millimeter.

Thus, FIG. 15 shows that the mean values presented in FIG. 5 may be a function of age, rather than fixed values. In other words, the mean values may decrease linearly as a function of age. In other embodiments, a more complex relationship may be established between the mean values and age. Similarly, where comparisons are made for a patient based on earlier collected samples, the effect of age may be included in these comparisons.

Thus, in one embodiment, the mean value of the vascular density per Ice Cube for a healthy retina is a function of age. As a result, one may create a reference curve, referred to as a healthy aging index, that shows the progression of mean value as a function of age. This healthy aging index may be used in determining thresholds used to determine the health of a retina, such as the thresholds used in FIG. 6.

Figure 16:
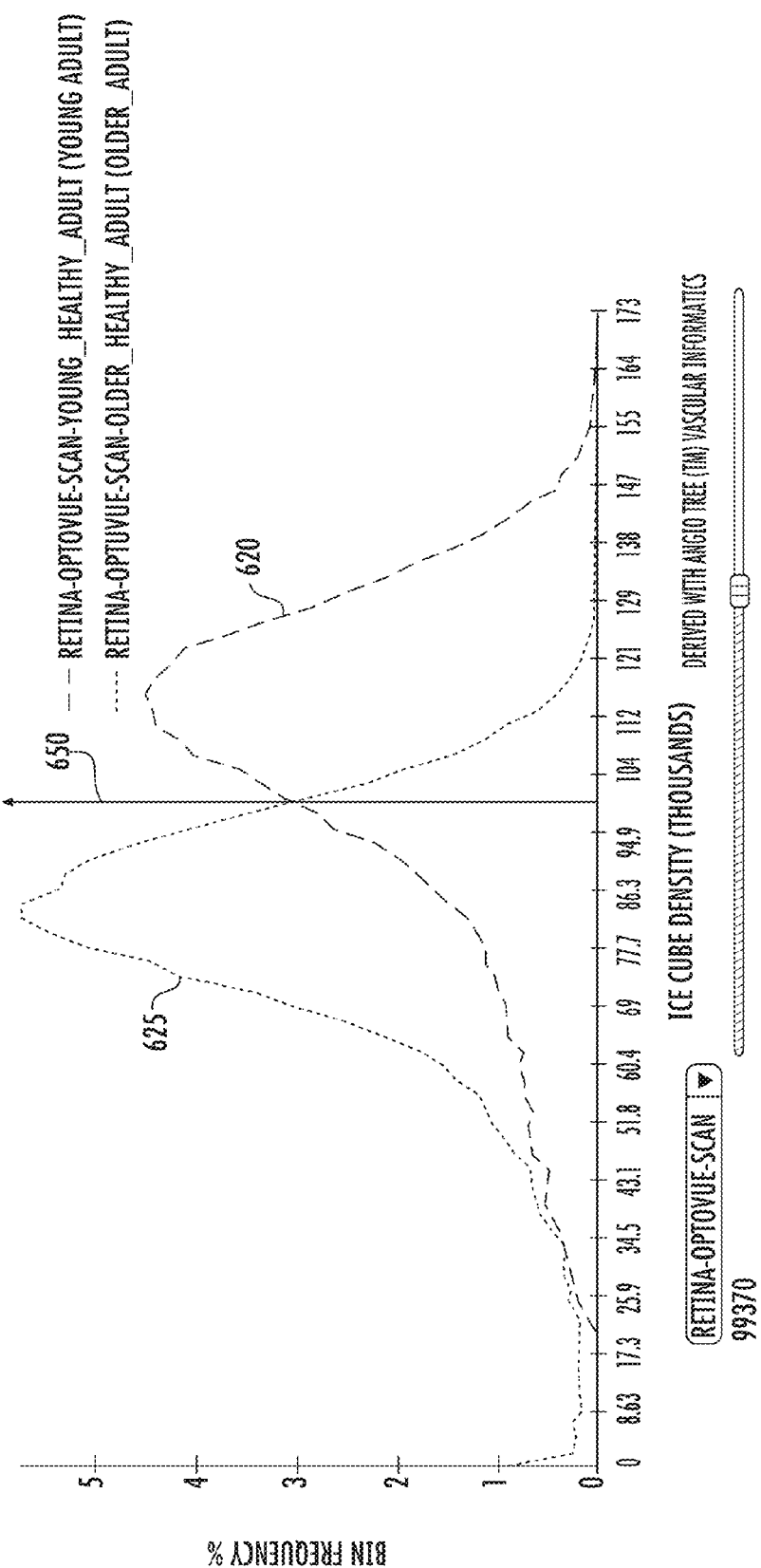
FIG. 16 shows the histogram of FIG. 15 with a threshold to define hot regions.
Figure 17:
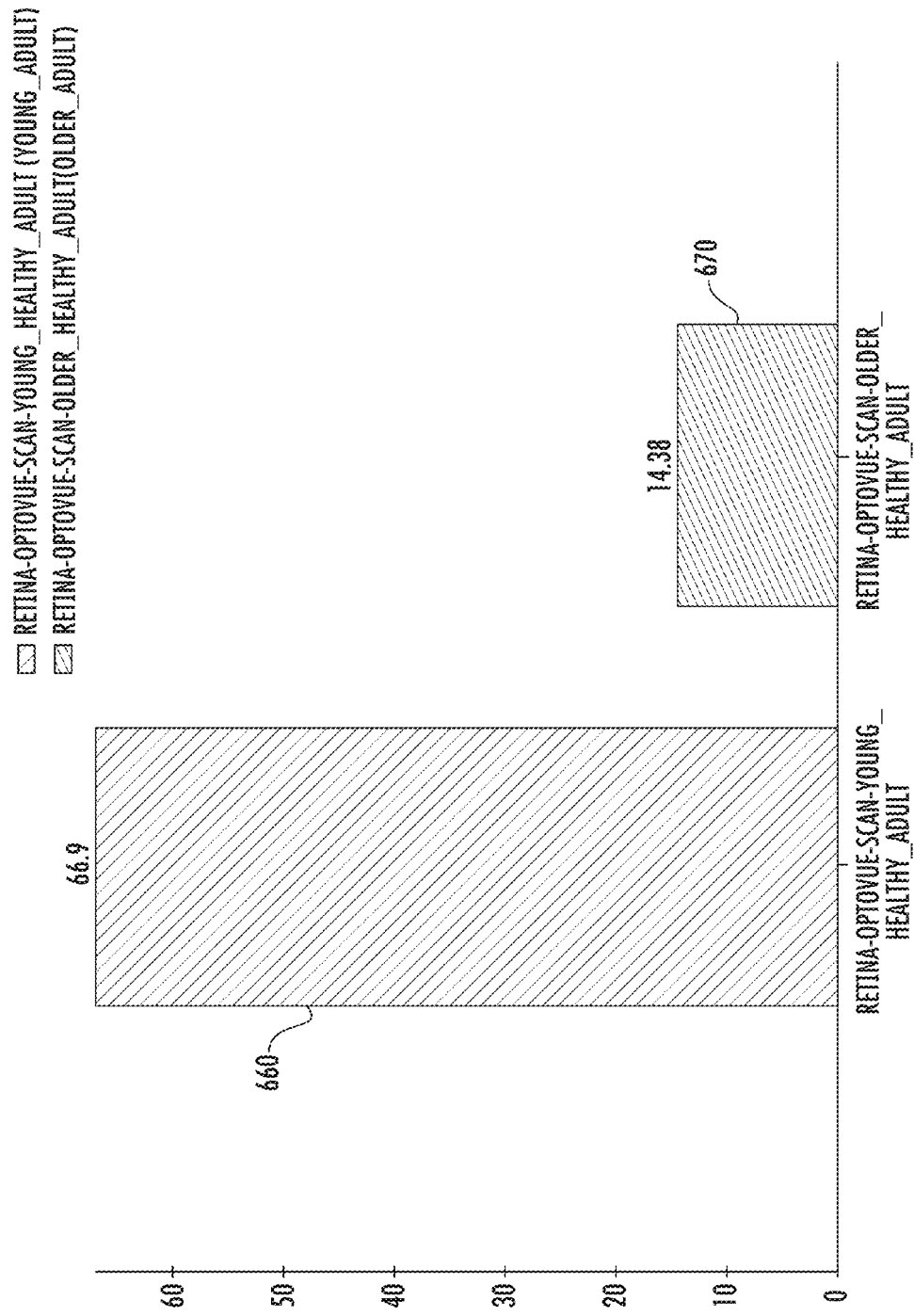
FIG. 17 shows the percentage of hot regions for the retinas of FIGS. 14A-14B.

FIG. 16 shows the histogram of FIG. 15 with a threshold value 650 added. This threshold value 650 may be located between the mean values shown in FIG. 15. In this particular figure, the threshold value 650 is 99,370 Poker Chips™/cubic millimeter. Using this threshold value 650 to distinguish the hot region, the bar graphs of FIG. 17 can be created.

Bar graph 660, which represents the data for the 27 year old patient, shows that 66.9% of the Ice Cubes are within the hot region. In contrast, bar graph 670, which represents the data for the 70 year old patient, shows that only 14.4% of the Ice Cubes are within the hot region.

In comparing FIG. 15 to FIG. 5, it can be seen that healthy aging affects the mean of the histogram, but does not greatly affect the shape. Lines 620, 625 both approximate bell curves, where the center of the bell curve shifts to the left as the patient ages in a healthy manner. In contrast, disease causes a change in the fundamental shape of the histogram, as shown in FIG. 5.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method of diagnosing disease in a retina, comprising:
   collecting a plurality of images of the retina;
   processing the plurality of images to create a 3D computer model, where blood vessels are modelled as a series of stacked disks;
   dividing the 3D model into a plurality of equally sized volumes;
   determining a vascular density in each equally sized volume based on a number of disks in each equally sized volume; and
   analyzing the vascular density in at least a portion of the equally sized volumes to determine the presence of a disease, wherein the portion of equally sized volumes comprises all equally sized volumes that are disposed in one plane.

2. The method of claim 1, wherein the analyzing comprises determining a mean vascular density and comparing the mean vascular density to a predetermined threshold.

3. The method of claim 1, wherein the analyzing comprises creating a histogram of vascular density vs. percentage of equally sized volumes.

4. The method of claim 3, wherein the analyzing further comprises comparing a shape of the histogram to a predetermined curve.

5. The method of claim 1, wherein the analyzing further comprises establishing a first threshold value and identifying the equally sized volumes that have a vascular density greater than the first threshold value as hot regions.

6. The method of claim 5, wherein the analyzing further comprises determining a percentage of equally sized volumes that are in the hot regions and comparing the percentage to a predetermined threshold.

7. The method of claim 5, wherein the analyzing further comprises establishing a second threshold value and identifying the equally sized volumes that have a vascular density less than the second threshold value as cold regions.

8. The method of claim 7, wherein the analyzing further comprises determining a first percentage of equally sized volumes that are in the hot regions and a second percentage of equally sized volumes that are in the cold regions, and comparing the first percentage and the second percentage to predetermined thresholds.

9. The method of claim 7, wherein the analyzing further comprises determining a first percentage of equally sized volumes that are in the hot regions and a second percentage of equally sized volumes that are in the cold regions, calculating a ratio of the first percentage to the second percentage and comparing the ratio to a predetermined threshold.

10. The method of claim 1, wherein the retina is divided into a plurality of annular rings, and the portion of equally sized volumes comprises all equally sized volumes that are disposed in at least one of the annular rings.

11. The method of claim 10, wherein the retina is also divided into a plurality of wedges, and the portion of equally sized volumes comprises all equally sized volumes that are disposed in at least one of the annular rings and disposed in at least one of the wedges.

12. The method of claim 1, wherein the retina is divided into a plurality of wedges, and the portion of equally sized volumes comprises all equally sized volumes that are disposed in at least one of the wedges.

13. A method of diagnosing disease in a retina, comprising:
collecting a plurality of images of the retina;
processing the plurality of images to create a 3D computer model, where blood vessels are modelled as a series of stacked disks;
dividing the 3D model into a plurality of equally sized volumes;
determining a vascular density in each equally sized volume based on a number of disks in each equally sized volume; and
analyzing the vascular density in at least a portion of the equally sized volumes to determine the presence of a disease, wherein the analyzing further comprises establishing a first threshold value and identifying the equally sized volumes that have a vascular density greater than the first threshold value as hot regions and establishing a second threshold value and identifying the equally sized volumes that have a vascular density less than the second threshold value as cold regions.

14. The method of claim 13, wherein the analyzing further comprises determining a percentage of equally sized volumes that are in the hot regions and comparing the percentage to a predetermined threshold.

15. The method of claim 13, wherein the analyzing further comprises determining a first percentage of equally sized volumes that are in the hot regions and a second percentage of equally sized volumes that are in the cold regions, and comparing the first percentage and the second percentage to predetermined thresholds.

16. The method of claim 13, wherein the analyzing further comprises determining a first percentage of equally sized volumes that are in the hot regions and a second percentage of equally sized volumes that are in the cold regions, calculating a ratio of the first percentage to the second percentage and comparing the ratio to a predetermined threshold.

17. The method of claim 13, wherein the portion of equally sized volumes comprises all equally sized volumes that are disposed in one plane.

18. A method of diagnosing disease in a retina, comprising:
collecting a plurality of images of the retina;
processing the plurality of images to create a 3D computer model, where blood vessels are modelled as a series of stacked disks;
dividing the 3D model into a plurality of equally sized volumes;
determining a vascular density in each equally sized volume based on a number of disks in each equally sized volume; and
analyzing the vascular density in at least a portion of the equally sized volumes to determine the presence of a disease, wherein the retina is divided into a plurality of annular rings, and the portion of equally sized volumes comprises all equally sized volumes that are disposed in at least one of the annular rings.

19. The method of claim 18, wherein the analyzing comprises determining a mean vascular density and comparing the mean vascular density to a predetermined threshold.

20. The method of claim 18, wherein the analyzing comprises creating a histogram of vascular density vs. percentage of equally sized volumes.

21. The method of claim 20, wherein the analyzing further comprises comparing a shape of the histogram to a predetermined curve.

22. The method of claim 18, wherein the retina is also divided into a plurality of wedges, and the portion of equally sized volumes comprises all equally sized volumes that are disposed in at least one of the annular rings and disposed in at least one of the wedges.

23. A method of diagnosing disease in a retina, comprising:
collecting a plurality of images of the retina;
processing the plurality of images to create a 3D computer model, where blood vessels are modelled as a series of stacked disks;
dividing the 3D model into a plurality of equally sized volumes;
determining a vascular density in each equally sized volume based on a number of disks in each equally sized volume; and
analyzing the vascular density in at least a portion of the equally sized volumes to determine the presence of a disease, wherein the retina is divided into a plurality of wedges, and the portion of equally sized volumes comprises all equally sized volumes that are disposed in at least one of the wedges.

24. The method of claim 23, wherein the analyzing comprises determining a mean vascular density and comparing the mean vascular density to a predetermined threshold.

25. The method of claim 23, wherein the analyzing comprises creating a histogram of vascular density vs. percentage of equally sized volumes.

26. The method of claim 25, wherein the analyzing further comprises comparing a shape of the histogram to a predetermined curve.

* * * * *